United States Patent [19]

Salem et al.

[11] Patent Number: 4,892,933
[45] Date of Patent: Jan. 9, 1990

[54] MONOCLONAL ANTIBODY FOR COLORECTAL CARCINOMA

[75] Inventors: Ronald R. Salem, Brookline; Peter Thomas, Pembroke; Norman Zamcheck, W. Newton; Glenn Steele, Swampscott, all of Mass.

[73] Assignees: New England Deaconess Hospital Corporation; Mallory Institute of Pathology Foundation, both of Boston, Mass.

[21] Appl. No.: 183,831

[22] Filed: Apr. 20, 1988

[51] Int. Cl.$^4$ .......................... C07K 15/00; C12N 5/00
[52] U.S. Cl. ............................... 530/387; 435/240.27; 435/70.21; 435/172.2; 435/948; 530/808; 530/809; 436/548; 935/104; 935/110
[58] Field of Search .................. 530/387, 388, 395; 435/240.27, 68, 172.3, 7; 424/85.8, 85.91; 436/548; 935/100, 104, 107, 108, 110

[56] References Cited

U.S. PATENT DOCUMENTS 4,363,799  12/1982  Kung et al. ........................... 424/85

OTHER PUBLICATIONS

Salem, R. R. et al. (I), "Production and Evaluation of a Monoclonal Antibody to Non-CEA-Producing Colorectal Cancers", Surgical Forum, Oct. 1987, pp. 408–410.
Salem et al (II), "Production and Evaluation of a Monoclonal Antibody to Non (EA Producing Colorectal Cancers (CRC)", Proc. Am. Assoc. Cancer Res. Annu. Meet, 28:396, 1987.
DeLellis et al. (1987), Seminars in Oncology 14:173–192.
Niles et al. (1987), Cancer Investigation 5:545–552.
Schoentag et al. (1987), Cancer Research 47:1695–1700.
Vecchi et al. (1987), Proc. Natl. Acad. Sci. USA 84:3425–3429.
Abe, et al. (1986), Cancer Research 46:2639–2644.
Bleday et al. (1986), Cancer 57:433–440.
itzkowitz et al. (1986), Cancer Research 46:2627–2632.
Rogers et al. ((1986), Cancer Immunol. Immunother. 23:107–112.
Sakamoto et al. (1986), Cancer Research 46:1553–1561.
Yuan et al. (1985), Cancer Research 45:4499–4511.
Nadakavukaren et al. (1984), Differentiation 27:209–220.
Fredman et al. (1983), The Journal of Biological Chemistry 258:11206–11210.
Wagener et al. (1983), The Journal of Immunology 130:2308–2315.
Herlyn et al. (1982), Proc. Natl. Acad. Sci. USA 79:4761–4765.
Kurzinger et al. (1982), The Journal of Biological Chemistry 257:12412–12418.
Goslin et al. (1981), The American Journal of Medicine 71:246–253.
Hsu et al. (1981), The Journal of Histochemistry and Cytochemistry 29:1349–1353.
Kupchik et al. (1981), Cancer Research 41:3306–3310.
Morrison (1980) Methods in Enzymology 70:214–220.
Herlyn et al. (1979), Eur. J. Immunol. 9:657–659.
Springer et al. (1979), Journal of Surgical Oncology 11:95–106.
Eye et al. (1978) Biochemistry 15:429–436.
Springer et al. (1977) Clinical Immunology and Immunopathology 7:426–441.
Search Report (Paper Chase) Relating Generally to the Field of Tumor-Specific Antigens.
Salem et al. (1987), Surgical Forum (Oct.), pp. 408–410.
Salem et al. (1987), Proceedings of AACR, vol. 28-Immunology, Abstract No. 1571.

Primary Examiner—Margaret Moskowitz
Assistant Examiner—Kay E. Cheney
Attorney, Agent, or Firm—Lahive & Cockfield

[57] ABSTRACT

A monoclonal antibody raised to colorectal carcinoma, and a hybridoma which elicits the antibody, have been produced. This antibody, ND4 has been discovered to react with a new tumor marker, a glycoprotein of approximately 160 kD found on the surface of undifferentiated colorectal carcinoma cells; it does not cross-react with other known tumor markers. It is useful for detecting and monitoring colorectal carcinoma.

9 Claims, No Drawings

MONOCLONAL ANTIBODY FOR COLORECTAL CARCINOMA

BACKGROUND OF THE INVENTION

The U.S. Government has rights in this invention pursuant to National Cancer Institute Grant Nos. CA 04486, CA 44583 and CA 44704.

The present invention relates to the field of cancer diagnosis, and more specifically to the identification of new cancer markers and monoclonal antibodies useful in the diagnosis, detection, and monitoring of human colorectal carcinoma.

Colorectal carcinoma is a cancer which affects many people per year. The prognosis is poor in about 50% of the cases because the tumor is often not detected until the disease has spread and has reached a terminal stage. Early diagnosis is important to increase chances of arresting the carcinoma before it metastasizes, thereby leading to an improved prognosis.

A widely used method of the identification of cancerous tissue is to determine its structural resemblance to fetal or immature tissue. In this way, tumors can be classified depending on the degree of cellular differentiation; they can be undifferentiated, poorly differentiated, moderately differentiated or well differentiated. In addition, the behavior of a given tumor can often be related to its degree of differentiation. For example, poorly differentiated tumors tend to grow more rapidly and metastasize earlier than do differentiated tumors which more closely resemble the tissue of origin. Poorly differentiated tumors tend to have a poor prognosis and are difficult to detect.

One method of early tumor diagnosis is detection of the presence of a marker or antigen specific for a particular tumor. These normally proteinaceous markers are synthesized by the tumor, and may be found in the serum and/or on the surface of the tumor. Only a limited number of tumor markers for colorectal carcinoma have thus far been found to have clinical use. These include carcinoembryonic antigen (CEA), and the sialyated Lewis a antigen (CA 19.9). Unfortunately, approximately 40% of patients whose condition has been accurately diagnosed as colorectal carcinoma do not have elevated plasma levels of either of these antigens when initially examined. There is no commercially available serodiagnostic marker which can be used to detect the tumor and to monitor therapy for this group.

production of some tumor markers e.g., CEA and CA 19.9, by tumor cells in vitro correlates with a greater degree of cellular differentiation. For example, CEA and CA 19.9 are present to a far lesser degree on poorly differentiated or undifferentiated cancer cells than on those which are more differentiated. Accordingly, many patients with undifferentiated colorectal carcinomas never develop elevated serum levels of either of these markers, even in the terminal stages of the cancer. There is also considerable overlap between the presence of CA 19.9 and CEA, the patient with a normal CEA level and an elevated level of CA 19.9 being the exception rather than the rule. Therefore, new markers suitable for identifying and monitoring undifferentiated tumors would be of great value.

Accordingly, it is an object of this invention to provide a new marker for the detection of colorectal carcinoma.

It is another object of the invention to provide a new marker suitable for diagnosing and monitoring colorectal carcinoma, and in particular, undifferentiated or poorly differentiated colorectal carcinoma for which known characterizing markers are not present.

A further object of the present invention is to provide a method and kit for the detection and monitoring of colorectal carcinoma in patients using antibodies specific for markers on colorectal carcinoma cells.

Yet another object of the invention is to provide a hybridoma which produces a monoclonal antibody that recognizes both undifferentiated and poorly differentiated colorectal carcinoma cells.

A still further object is to provide screening procedures for detecting the presence of colorectal carcinoma cells at all stages of differentiation.

SUMMARY OF THE INVENTION

A monoclonal antibody raised to an undifferentiated tumor cell line has been found to react with a new tumor marker for human colorectal carcinoma (hereinafter referred to as the CC glycoprotein). This marker is a glycoprotein of approximately 160,000 daltons molecular weight, and is found on the surface of undifferentiated as well as more differentiated colorectal carcinoma cells.

This monoclonal antibody (referred to hereinafter as the ND4 antibody), is useful for detecting colorectal carcinoma of varying degrees of differentiation. The ND4 antibody may be produce by a hybridoma, or may be synthesized in whole or in part by recombinant means. It may also consist of a fragment or modified antibody, whether produced by a hybridoma or by a recombinant means, which is capable of reacting with the CC glycoprotein. The antibody to the marker does not cross-react with other tumor markers such as CEA, CA 19.9, alpha-1-acid glycoprotein, or NCA; nor does it cross-react with any of the blood group substances A, B, or H.

The hybridoma which elicits the ND4 monoclonal antibody is formed upon the fusion of a mouse myeloma cell, such as one from the NS-1 line, with a spleen cell from a mouse previously immunized with undifferentiated colorectal carcinoma cells. The immunogen may alternatively be the CC glycoprotein, or analogs or portions thereof.

The foregoing and other objects of the present invention, the various features thereof, as well as the invention itself may be more fully understood from the following description of the invention.

DESCRIPTION

The present invention relates to cancer detection. More particularly, this invention relates to an antibody which reacts with a newly discovered tumor marker found on the surface of colorectal carcinomas, such as those which are undifferentiated, and which otherwise would not have been detected with antibodies to other tumor markers.

The present invention also features a hybridoma cell line which produces the forementioned ND4 monoclonal antibody. This hybridoma is formed upon fusion of a mouse myeloma cell with a spleen cell from a mouse which had been previously immunized with undifferentiated or nondifferentiated tumor cells. Preferably, non-CEA and/or non-CA 19.9-producing and undifferentiated colorectal cancer cells such as MIP 101 cells are used as the immunizing agent. Alternatively, the immunogen may be the CC glycoprotein, analogs or portions thereof. The mice whose spleen cells were chosen for fusion are preferably from a genetically defined lineage such as Balb/c. The myeloma cells used in the fusion are from a mammalian, antibody-producing cell line, but most preferably are from a mouse cell line, an example being NS-1.

The monoclonal antibody of the present invention can be obtained from ascites fluid of mice injected with the forementioned hybridoma. The antibody is specific for tumor cells and many fetal tissues, as determined by fluorescence binding studies performed on formalin-fixed cells, and will recognize tumor cells having different degrees of differentiation including some CEA- and/or CA 19.9-producing cells. However, this antibody is particularly useful in recognizing tumor cells which are undifferentiated or poorly differentiated, and which do not elicit detectable levels of CEA and/or CA 19.9.

More particularly, the antibody of the present invention reacts with the CC glycoprotein, as demonstrated by its binding to that protein on sodium dodecyl sulfate (SDS)-polyacrylamide gels, and will react also with analogs or portions of the CC glycoprotein. It does not, however, cross-react with other known tumor markers such as CEA, CA 19.9, NCA, and alpha-1-acid glycoprotein, or with any of the blood group substances A, B, or H, as determined by established ELISA procedures.

The antibody of the present invention can be of any class and subclass, but that produced by the forementioned hybridoma was determined to be of the IgG2 subclass by the Ouchterlony double diffusion test. This antibody may also be synthesized by recombinant means, either in whole or in part, and may be linked to other functional molecules such as toxins, dyes, enzymes, or radioactive markers.

The following procedure demonstrates how the ND4 antibody can be utilized to isolate the CC glycoprotein from the undifferentiated, non-CEA-producing cell line MIP 101. Radiolabeled, undifferentiated MIP 101 tumor cells are first lysed with a detergent-containing buffer. The lysate is then subjected to immunoprecipitation procedures using the ND4 monoclonal antibody. Polypeptides in the immunoprecipitates are then separated by electrophoresis on polyacrylamide gels containing sodium dodecyl sulfate, and identified by autoradiography. Using this methodology, the marker was demonstrated to be a glycoprotein having a molecular weight of approximately 160,000 daltons. This marker has also be found on the surface of many CEA (+) and CEA (−) tumor cell lines.

The present invention further provides a method for detecting tumor cells, which includes contacting a biological sample with a receptor which is capable of reacting with the CC glycoprotein, analogs, and fragments thereof, and observing whether the receptor reacts with the sample.

Examples of biological samples which may be examined by this method include tissue biopsies, tumors, blood, serum, ascites fluid, tissue cultures, and histological preparations thereof. A histological preparation of a biological preparation may include a wet mount, a dry mount, a frozen sample, a parfffin-embedded sample, an acrylic-embedded sample, or a sample adapted in any way for microscopic examination.

The antibody may be a polyclonal antibody or portion thereof raised to undifferentiated tumor cells, and shown to react with the CC glycoprotein, analogs, and fragments thereof. However, the antibody is most preferably a monoclonal antibody or fraction thereof.

A reaction between the antibody and a sample may be detected by an assay including, for example, one which is enzyme-linked and one which is immunological. A preferred assay is an immunoassay such as a radioimmunoassay, Western blot, or a nitrocellulose "dot" blot.

The method of the present invention can be employed for diagnostic and prognostic purposes, for example, to monitor the growth of a tumor or the functional status of normal colorectal cells. More specifically, the method can be employed, for example, to diagnose the in vivo presence of tumor cells which are undifferentiated or poorly differentiated, and which do not produce CEA and/or CA 19.9.

This screening method can also be expanded to include the use of monoclonal antibodies which are specific for other tumor markers, such as CEA and CA 19.9, so as to enable the determination of the level of differentiation which a tumor cell has achieved. The presence of CEA or CA 19.9 has been correlated with higher degrees of differentiation while the presence of the CC glycoprotein has been correlated with both high and low degrees of differentiation. Therefore, a tumor cell which tests positively for the CC glycoprotein, but tests negatively for CA 19.9 and CEA is most likely undifferentiated or poorly differentiated.

The instant invention also relates to a method for screening patients for colorectal carcinoma. It includes subjecting a biological sample (as previously defined) to at least one test selected from a plurality of tests, each of which is specific for a colorectal carcinoma cell marker, and correlating the presence of a specific marker with a degree of differentiation of that cell.

The screening method of the present invention includes tests for tumor markers CEA, CA 19.9, NCA, alpha-1-acid glycoprotein, and the CC glycoprotein, as well as any additional markers which indicate the presence of colorectal carcinoma. The tests performed may be assays, for example, to determine enzyme-linked activity, or may be immunoassays which utilize an antibody specific for a particular marker. They may be performed in a sequential manner until the presence of at least one marker has been proven.

Finally, this invention provides a convenient kit for screening biological samples for colorectal carcinoma. This kit includes antisera or antibodies specific for tumor markers such as the CC glycoprotein, NCA, CA 19.9, CEA, alpha-1-acid glycoprotein, and may also include any other relevant antisera or antibodies. Screening may be performed by any immunoassay procedures such as, for example, radioimmunoassay, Western blot analysis, or nitrocellulose "dot" analysis.

The following examples illustrate the best mode of making and practicing the present invention, but are not meant to limit the scope of the invention, since alternative methods may be used to obtain similar results.

EXAMPLE 1

Hybridome and Monoclonal Antibody Production

Balb/c mice (The Jackson Laboratory, Bar Harbor, Me; 6-8 weeks old) were immunized with four injections of MIP 101 cells, a colorectal cancer cell line of undifferentiated morphology (Niles, et al., Cancer Invest., in press (Dec., 1987)). The injections were performed one week apart and $5 \times 10^6$ cells were injected on each occasion. The first three injections ever given intraperitoneally, and the fourth intravenously, Cells were injected with complete Freunds adjuvant on the first occasion, incomplete adjuvant on the second and third occasions, and without adjuvant on the last occasion. Serum withdrawn prior to the last injection showed prominent binding to both the immunogen (MIP 101 cells) and another poorly differentiated cell line, Clone A (derived from DLD-1 (ATCC No. CCL221) by D. Dexter, Roger Williams Hosp., Providence, R.I., now at DuPont, Wilmington, Del.) using a solid phase microtiter plate enzyme-linked immunoassay. The mouse with the best immune response was sacrificed three days after the last injection.

Hybridomas were produced by fusion of spleen cells from the sacrificed mouse with NS-1 (P3NS-1/1-Ag4-1) myeloma cells (American Type Culture Collection, Rockville, Md.; Acc. No. TIB18). In the present example, the method of Nadakavukaren (*Differentiation* 27: 209–202. (1984)) was employed to perform the fusions. Resultant clones were tested for binding to MIP 101 cells and to Clone A. Subcloning by serial dilution was carried out on one clone. The most productive subclone was injected into the peritoneal cavity of Balb/c mice to produce ascites fluid containing monoclonal antibody. The hybridoma (ND4) which produces this subclone was deposited with the American Type Culture Collection (1203 Parklawn Drive Rockville, Md. 20852; ATCC No. HB 9600) on 12/8/87. The ascites fluid obtained was centrifuged, tested for activity, and then stored at −70° C. until required. This source of monoclonal antibody, designated ND4, was used in all subsequent investigations.

EXAMPLE 2

Characterization of Resulting Monclonal Antibodies

A. Binding of Monoclonal Antibodies to Cell Lines In Vitro.

Binding studies were performed on formalin-fixed cells using the ND4 antibody and rhodamine conjugated rabbit anti-mouse antiserum. In the present example, the method of Bleday et al. (Cancer 57: 443–440, (1986)) was followed. Cells were viewed to determine binding using a Zeiss epiflourescent microscope. Twenty eight different cell lines were examined; fifteen human colorectal lines, including nine which produced CEA and six which did not (Table 1); seven human, non-colorectal carcinoma lines (Table 2); and six normal, non-human cell lines (Table 2). Ascites fluid from an IgG2a-producing mouse myeloma line UPC-10 (Sigma) was used as a negative control antibody. Binding to cell lines was graded "−," "+" or "++" dependant on degree of fluorescence. Cell lines were obtained from several sources. All CCL lines, MCF-7, CRL 1420, CV-1, and A431 were obtained from the American Type Culture Collection. CX-1 was obtained from S. Bernal (Dana-Faber Cancer Institute, Boston, Mass.); Moser was from M. Brattain (Baylor College of Medicine, Houston, Tex.); and EJ, RT112 and MB49 were from I. Summerhayes (New England Deaconess Hospital, Boston, Mass). DLD-2 and DLD-1-derived Clones A and D were obtained from D. Dexter (Roger Williams Hospital, Providence, R.I., now at Dupont, Wilmington, Del.).

TABLE 1

| HUMAN COLORECTAL CARCINOMA LINE | CEA PRODUCTION (ng/$10^6$ cells/ml) | ND4 IMMUNO-FLUORESCENCE |
|---|---|---|
| CCL 235 | 523 | + |
| CCL 238 | 362 | ++ |
| DLD 2 | 120 | + |
| CX1 | 70 | ++ |
| CCL 222 | 2.5 | ++ |
| CCL 228 | 0.7 | − |
| CCL 231 | 0.6 | ++ |
| CCL 227 | 0.15 | ++ |
| MOSER | (+) | ++ |
| CCL 220 | 0.0 | ++ |
| CCL 220.1 | 0.0 | ++ |
| CCL 224 | 0.0 | ++ |
| MIP 101 | 0.0 | ++ |
| CLONE A | 0.0 | ++ |
| CLONE D | 0.0 | ++ |

TABLE 2

| CELL LINE | ND4 TISSUE SOURCE | IMMUNO-FLUORESCENCE |
|---|---|---|
| CRL 1420 | Human Pancreatic Cancer | − |
| MCF7 | Human Breast Cancer | ++ |
| EJ | Human Bladder Cancer | − |
| RT 112 | Human Bladder Cancer | − |
| A431 | Human Vulval Cancer | − |
| CCL 105 | Human Adrenal Cancer | + |
| CCL 185 | Human Lung Cancer | − |
| LOX | Human Melanoma | − |
| KAPOSI | Human Sarcoma | − |
| CV-1 | Normal Monkey Kidney | − |
| MB49 | Normal Mouse Bladder | + |
| THE | Normal Hamster Stomach | − |
| F111 | Normal Rat Fibroblast | − |
| A31 | Normal Mouse Fibroblast | − |
| CCL 22 | Normal Bovine Kidney | − |

After formalin fixation, indirect. immuofluorescence showed rhodamine-conjugated antibody binding to 14 out of 15 human colorectal carcinoma cell lines, with prominent (++) binding to 12 out of 15 (80%) lines. Prominent binding was also seen on all of the 6 non-CEA-producing colorectal carcinoma cell lines. Two of seven human, non-colorectal carcinoma lines and one of six nonhuman lines also bound the antibody.

B. Immunohistopathology.

Immunohistopathological studies were performed to determine whether the ND4 antibody binds to a cancerous or normal human tissue and if so, on which cells in the tissue section.

Formalin-fixed, paraffin-embedded tissue sections were deparaffinized with xylene and ethanol, rehydrated, and incubated with phosphate buffered saline (PBS) containing 0.3% $H_2O_2$ to block endogenous peroxidase activity. Sections were washed and blocked with 1% horse serum for 30 minutes and then incubated at 4° C. overnight with ND4 antibody. Subsequent staining was performed according to a standard avidin-biotin-immunoperoxidase technique. In the present example, the method of Hsu et al. ((1981) Cytochem. 29:1349–1353) was followed. Tissue specimens were obtained from the Department of Surgery, Deaconess Hospital, Boston, MA or the Department of Pathology, Boston City Hospital, Boston, Mass.

The following tissues were examined: colon carcinoma, including two well differentiated, nine moderately differentiated, and four poorly differentiated or undifferentiated tumors; normal tissue from thirteen different specimens of normal colonic mucosa obtained from patients with either benign colonic diseases or entirely normal colons, or from the margin of colonic resections from patients who had undergone surgery for colorectal cancer; twenty one different normal non-colonic tissue samples obtained by autopsy; and samples from eleven non-colonic tumors, of which two were gastrointestinal in origin. The results are shown in Table 3.

TABLE 3

BINDING OF ND4 MONOCLONAL ANTIBODY TO COLORECTAL CARCINOMA.

| TISSUE | NO. of SAMPLES | % OF SAMPLES BINDING |
| --- | --- | --- |
| Colorectal carcinomas (including 3 of 4 poorly differentiated tumors) | 15 | 60% |
| Normal colonic epithelium | 13 | 15% |
| Normal non-colonic tissue | 21 | 5% |
| Non-colonic tumors | 11 | 9% |

B. Antibody Typing.

ND4 antibody was screened for antibody isotype by the Ouchterlony double diffusion test in agar plates against anti IgM, anti IgG, anti IgG1, anti IgG2a, anti IgG2b and anti IgG3 antibodies (Cappell). Precipitating bands were produced only with anti-IgG2a antibodies.

EXAMPLE 3

CC Glycoprotein Isolation

Antigen characterization was performed by immunoprecipitation of MIP 101 cells which had been radio labelled by three different procedures. Cells were labelled overnight with [$^{35}$S]-methionine, or with [$^{3}$H]-glucosamine (New England Nuclear) according to the method of Kurzinger et al. (J.B.C. 257: 20,12412–12418, (1982)). Cell surfaces of live MIP 101 cells were labelled with $^{125}$Iodine using the lactoperoxidase procedure of Morrison (Methods Enzymol. 70: 214–220 (1980)). The labelled cells were lyzed in RIPA buffer containing 150 mM sodium chloride, 1% Triton-X-100 (Sigma), 0.1% sodium dodecyl sulfate (SDS; Biorad) and 10 mM Tris-HCl PH 7.2, to which 1 mM phenylmethylsulphonyl fluoride (Sigma) was added. Immunoprecipitations were carried out using protein A-Sepharose (Sigma) to which a goat-anti-mouse whole serum immunoglobulin (Cappell) was linked. The cell lysate was preincubated at 4° C. with the protein A complex. Immunoprecipitations with ND4 antibody were carried out as previously described (Hsu et al. Cytochem. 29: 1349–1353) 1981)). Precipitations with UPC-10 (Sigma) or without antibody were used as negative controls. Immunoprecipitates were analyzed by SDS-polyacrylamide gel electrophoresis on 10% gels, followed by autoradiography of the dried gels with Kodak X-OMat film. For the [$^{35}$S]-methionine and [$^{3}$H]-glucosamine-labelled cells, the gels were soaked in EnHance (Dupont) for 45 minutes, and were then washed in distilled water for 30 minutes prior to drying and exposure to X-ray film.

Immunoprecipitation of antigen labelled with $^{125}$Iodine, [$^{35}$S]-methionine and [$^{3}$H]-glucosamine each showed a band of approximately 160,000 daltons molecular weight on SDS-polyacrylamide gels. This band was absent when either control antibody or no antibody was used.

EXAMPLE 4

Characterization of CC Glycoprotein

Effect of Trypsin on ND4 Antibody Binding.

To determine if the marker recognized by the ND4 antibody were a protein, MIP 101 cells which were known to have this marker were pretreated with the serine protease, trypsin, to determine if recognition would be affected. Ninety six well, sterile ELISA microtiter plates were seeded with MIP 101 cells which were grown until confluent Cells were then fixed with 40% formaldehyde at 24° for 15 minutes, and then rinsed twice in PBS. Two lanes of cells were incubated with 1% trypsin (Gibco) at 37° for two hours and two lanes were incubated with PBS as positive controls. All lanes were examined by light microscopy to ensure that cells had not detached from the microtiter plate. Trypsin-treated and PBS-treated wells were incubated for one hour at 37° C with ND4 antibody in serial dilutions from 1:100 to 1:100,000. The plates were washed and then incubated with peroxidase-conjugated goat-anti-mouse immunoglobulin (Hyclone). After further washes the plates were developed using orthophenyline diamine as a substrate. The plates were read in a Biorad EIA reader at an absorbance of 492 nm. Optical density was plotted against ND4 antibody dilution for both trypsin-treated and PBS-treated lanes.

Trypsin treatment of formalin-fixed MIP 101 cells resulted in loss of >90% of the binding of ND4 antibody to the cells, as determined by the ELISA, indicating that the antigen recognized by the ND4 antibody is present as a polypeptide residing on the surface of MIP 101 cells.

B. Cross-Reactivity with Other Antigens.

Purified CEA, NCA, and alpha-1-acid glycoprotein as well as blood group antigens obtained from saliva of patients of AB and 0 blood types were bound to wells of ELISA microtiter plates using 0.1 bicarbonate buffer, pH 9.6. After blocking with 3% bovine serum albumen in Tris-buffered saline for one hour at 37° C., the wells were incubated with ND4 antibody and antibodies to blood group substances A, B, and H as positive controls for the saliva-derived antigens. Subsequent reactions were carried out as described for the ELISA procedure mentioned above.

No cross-reactivity of the ND4 antibody with CEA, NCA, or alpha-1-acid glycoprotein, or with any of the blood group antigens A, B and H was detected by this test.

EXAMPLE 5

Antigen Detection in Patients with Colorectal Cancer

Ascites fluid from two patients, serum from 37 patients with colorectal cancer and serum from 11 normal subjects were assayed for the presence of the CC glycoprotein antigen using a nitrocellulose "dot" immunossay. Nine of the patients had early stage disease. Five microtiter "dots" of 1:5 dilutions of ND4 antibody-containing ascites fluid or serum in PBS were placed on a nitrocellulose membrane. After allowing these dots to air dry, the membrane was blocked with 3% bovine serum albumen for one hour at 20° C. The membrane was incubated with a 1:100 dilution of ascites fluid at 4° C. overnight, washed with PBS, and incubated with sheep-anti-mouse IgG that had been preabsorbed with a mixture of polymerized whole serum and human IgG (Cappell) for two hours at 20° C. The reaction was developed with 4-chloro-2-napthol and H$_2$O$_2$.

Nitrocellulose dot immunoassays of serum from patients with colorectal cancer showed positive reactions in 15 of 37 patients (41&). Three patients had early stage disease and had CEA levels of less than 2.5 ng/ml.

Three patients with positive assays prior to resection of their primary tumor had negative reactions postoperatively.

As illustrated by the forementioned examples, a hybridoma-derived monoclonal antibody which reacts with a newly discovered tumor marker, CC glycoprotein has been produced, characterized, and successfully employed to detect colorectal carcinomas which may otherwise would not have been detected with antisera specific for other tumor markers.

The invention may be embodied in other specific forms without departing from the spirit or essential characteristics thereof. The present embodiments are therefore to be considered in all respects as illustrative and not restrictive, the scope of the present invention being indicated by the appended claims rather than by the foregoing description, and all the changes which come within the meaning and range of equivalency of the claims are therefore intended to be embraced therein.

We claim:

1. A monoclonal antibody characterized by specifically binding to the CC glycoprotein, said glycoprotein being a surface marker for a plurality of human colorectal carcinomas and having a molecular weight of approximately 160,000 daltons.

2. The monoclonal antibody of claim 1 wherein said antibody is further characterized by not specifically binding with tumor markers selected from the group consisting of CEA, CA 19.9, alpha-1-acid glycoprotein, NCA, and not specifically binding with any of the blood group substances A, B and H.

3. The monoclonal antibody of claim 1 wherein said monoclonal antibody is produced by a hybridoma, said hybridoma being a fusion product of a mouse myeloma cell and a spleen cell from a mouse previously immunized with undifferentiated human colorectal carcinoma cells that express the CC glycoprotein on their surfaces.

4. A hybridoma which produces a monoclonal antibody that specifically binds the CC glycoprotein, said glycoprotein having a molecular weight of 160,000 daltons, being found on the surface of undifferentiated colorectal carcinomas cells, and not specifically binding with any of CEA, CA 19.9, alpha-1-acid glycoprotein, NCA, or with blood group substances A, B, and H.

5. The hybridoma of claim 4 wherein said hybridoma is a fusion product of a mouse myeloma cell and a spleen cell from a mouse previously immunized with undifferentiated human colorectal carcinoma cells that express the CC glycoprotein on their surfaces.

6. The hybridoma of claim 5 wherein said mouse had previously been immunized with CC glycoprotein, analogs, or fragments thereof.

7. The hybridoma of claim 5 wherein said myeloma cells comprise cells from the NS-1 line.

8. A hybridoma according to claim 4 designated ATCC HB 9600.

9. Monoclonal antibody ND4 produced by the hybridoma of claim 8.

* * * * *